United States Patent
Iehl et al.

(10) Patent No.: US 11,141,206 B2
(45) Date of Patent: Oct. 12, 2021

(54) BONE SUBSTITUTE AND INDEPENDENT INJECTION SYSTEM

(71) Applicant: TEKNIMED, Vic-en-Bigorre (FR)

(72) Inventors: Julien Iehl, Tournefeuille (FR); Gautier Halbin, Toulouse (FR); Cyril Sender, Toulouse (FR); Nouredine Sahraoui, Toulouse (FR)

(73) Assignee: TEKNIMED, Vic-en-Bigorre (FR)

( * ) Notice: Subject to any disclaimer, the term of this patent is extended or adjusted under 35 U.S.C. 154(b) by 225 days.

(21) Appl. No.: 16/314,111

(22) PCT Filed: Jun. 30, 2017

(86) PCT No.: PCT/EP2017/066346
§ 371 (c)(1),
(2) Date: Dec. 28, 2018

(87) PCT Pub. No.: WO2018/002335
PCT Pub. Date: Jan. 4, 2018

(65) Prior Publication Data
US 2019/0216515 A1    Jul. 18, 2019

(30) Foreign Application Priority Data

Jun. 30, 2016  (FR) ...................................... 1656231

(51) Int. Cl.
*A61B 17/88* (2006.01)
*A61L 27/46* (2006.01)
(Continued)

(52) U.S. Cl.
CPC ...... *A61B 17/8805* (2013.01); *A61B 17/8802* (2013.01); *A61B 17/8836* (2013.01);
(Continued)

(58) Field of Classification Search
CPC ........................ A61B 17/8805; A61B 17/8836
See application file for complete search history.

(56) References Cited

U.S. PATENT DOCUMENTS

| 637,405 | A | * | 11/1899 | Papendell | ........... | A61M 5/3158 604/208 |
| 7,077,826 | B1 | * | 7/2006 | Gray | ................... | A61M 5/3135 604/171 |

(Continued)

FOREIGN PATENT DOCUMENTS

| JP | 2004-500963 A | 1/2004 |
| JP | 2005-510291 A | 4/2005 |

(Continued)

OTHER PUBLICATIONS

International Search Report (PCT/ISA/210) issued in PCT/EP2017/066346, dated Jul. 26, 2017.
(Continued)

*Primary Examiner* — Nicholas W Woodall
(74) *Attorney, Agent, or Firm* — Birch, Stewart, Kolasch & Birch, LLP (57) ABSTRACT

The invention relates to the field of bioresorbable or non-bioresorbable bone substitutes to be implanted in humans in order to reconstitute the bone supply by replacing lost bone substance. More particularly, the invention concerns a device that is simple to manufacture and use and comprises a syringe provided with a single-use dose of a polymer which is fluid at the injection temperature while being solid and durable at body temperature.

17 Claims, 1 Drawing Sheet

(51) Int. Cl.
*A61L 27/16* (2006.01)
*A61L 27/12* (2006.01)
*A61F 2/46* (2006.01)

(52) U.S. Cl.
CPC .............. *A61L 27/12* (2013.01); *A61L 27/16* (2013.01); *A61L 27/46* (2013.01); *A61F 2/4601* (2013.01); *A61L 2400/06* (2013.01); *A61L 2430/02* (2013.01)

(56) References Cited

U.S. PATENT DOCUMENTS

| | | | | |
|---|---|---|---|---|
| 8,366,717 | B1* | 2/2013 | Jordan | A61B 17/864 606/94 |
| 9,554,839 | B2* | 1/2017 | Lin | H05B 3/42 |
| 2004/0010313 | A1* | 1/2004 | Aston | A61L 31/088 623/17.11 |
| 2004/0230309 | A1* | 11/2004 | DiMauro | A61L 27/3821 623/17.12 |
| 2005/0245938 | A1 | 11/2005 | Kochan | |
| 2007/0191963 | A1 | 8/2007 | Winterbottom et al. | |
| 2007/0299426 | A1 | 12/2007 | Trieu et al. | |
| 2008/0249530 | A1 | 10/2008 | Truckai et al. | |
| 2008/0269761 | A1* | 10/2008 | Truckai | A61B 17/8805 606/94 |
| 2008/0300540 | A1* | 12/2008 | Lewis | A61B 17/8836 604/114 |
| 2010/0030220 | A1 | 2/2010 | Truckai et al. | |
| 2010/0211058 | A1 | 8/2010 | Winterbottom et al. | |
| 2011/0202063 | A1 | 8/2011 | Bonnin et al. | |
| 2012/0130386 | A1 | 5/2012 | McKay | |
| 2013/0218291 | A1* | 8/2013 | Giorno | A61L 27/3691 623/23.51 |

FOREIGN PATENT DOCUMENTS

| | | |
|---|---|---|
| WO | WO 02/000143 A1 | 1/2002 |
| WO | WO 03/045274 A2 | 6/2003 |
| WO | WO 2007/028120 A2 | 3/2007 |

OTHER PUBLICATIONS

Written Opinion (PCT/ISA/237) issued in PCT/EP2017/066346, dated Jul. 26, 2017.

* cited by examiner

BONE SUBSTITUTE AND INDEPENDENT INJECTION SYSTEM

TECHNICAL FIELD OF THE INVENTION

The present invention relates to the field of bioresorbable or non-bioresorbable bone substitutes to be implanted in humans in order to reconstitute the bone supply by replacing lost bone substance.

The invention more particularly relates to the field of bone filling under mechanical stress.

PRIOR ART

Osteoporosis is a major medical problem, and increasingly a major economic problem. Over a third of women and about one in seven men of age 50 will present a fracture secondary to osteoporosis once in their life.

Fracture of the vertebral body is the most common. The first percutaneous vertebroplasty was performed in 1984. Galibert et al. treated a cervical vertebral angioma by transcutaneous puncture and filling of the vertebral body with a polymethyl-metacrylate (PMMA) cement. For several years now, vertebroplasty has increasingly been accepted in the treatment of osteoporotic vertebral fractures.

Vertebroplasty consists in percutaneously injecting a cement, for example acrylic, into the vertebral bodies under fluoroscopic and/or tomographic monitoring. The vertebroplasty method was perfected in order to restore the generally wedged vertebral body to its original form. Kyphoplasty consists in dilating (i.e. reducing) the vertebral body by means of an inflatable balloon before injecting the cement.

These techniques make it possible to ease pain, reduce painkiller use, and shorten hospitalization. In the 72 hours following vertebroplasty, 85 to 90% of patients with osteoporotic vertebral fractures have a remarkable reduction or even complete elimination of their pain.

Acrylic resins have a high mechanical strength of about 80 to 90 MPa in compressive strength, and are used in these techniques for bone filling under stress. However, PMMA cement has several disadvantages. It is recognized that the in vivo hardening of PMMA cements generates free radicals. Moreover, the polymerization reaction of these materials when prepared extemporaneously in the operating theater is exothermic and the heat generated during curing is high, exceeding 90° C., and can damage surrounding tissues. Resorbable and biocompatible bone substitutes such as calcium phosphate ceramics, bioglasses, and other implantable medical devices available in the form of blocks or pellets have insufficient mechanical strength. Calcium phosphate cements, in spite of curing in situ and having a mechanical strength of 4 to 20 MPa for the most resistant, also do not meet the specifications for bone filling techniques under stress. In addition, the curing of these polymers is irreversible and once initiated, the surgeon has only a small time window for injection. Also, if the surgeon must interrupt the injection for one reason or another and the cavity to be filled is not filled, the surgeon must start all over and discard the injection equipment containing the cured polymer.

The development of bone substitutes combining a calcium phosphate ceramic type or bone type agent with one or more bioresorbable polymers has been observed.

For example, EP2395949 describes a bone substitute material which is liquid or pasty when heated to a temperature of 70 to 95° C. and is thus extrudable and injectable into an implantation site. After cooling, the material solidifies and is resorbed, leaving room for bone tissue. It is further stated that the invention described in EP2395949 is based on the principle of heating a bone substitute which becomes fluid at an elevated temperature by means of a device used to administer said heated material.

Numerous combinations are described, such as bone/polymer composites, mineral/polymer composites, ceramic/polymer composites. The polymer can be polycaprolactone, poly(lactide-co-glycolide), or polyurethane. Examples of composite bone substitute materials are described with reference to documents US2005/0008672, WO04/53112, WO2007/084725, US2008/0069852, and US2007/0191963. These documents describe osteoimplants comprising a combination of polymers of various origins and chemical natures associated with a bone derivative, an inorganic material, a bone substitute material, or a combination thereof.

WO2003/059409 discloses an implant comprising an anhydrous calcium sulfate supplemented with a bioresorbable polymer and calcium phosphate. The bioresorbable polymer may be a polymer or copolymer of lactic acid, of glycolic acid, of hydroxybutyric acid, of hydroxyvaleric acid, of polydioxane, of polycaprolactone, of polyethylene oxide, or polyethylene terephthalate. However, that document does not disclose an implant suitable for use by heating to a temperature of about 60° in order to melt it or at least soften it to enable its extrusion and administration at a particular point in bone.

US2008/0003255 describes thermoplastic materials for bone repair. Aliphatic polyesters are described therein as suitable materials, and polycaprolactone in particular. It is stated that polycaprolactone having a molecular weight of more than 100,000 has a melting point of about 60° C., which allows it to be injected. It is also indicated that this material can be heated and injected using a heat gun equipped with a resistive heater and temperature control loop.

U.S. Pat. No. 8,562,619 describes a method, a material, and a device for injecting said material for bone filling and/or repair. The method described consists in heating a bone cement composition in order to render the composition fluid, then injecting it into the area to be filled so that it solidifies there. It is indicated that the injection temperature is lower than that of the original melt to prevent necrosis, but the fluid state is still maintained. It is indicated that the bone cement composition comprises a thermoplastic biocompatible polymer the melting point of which is between 70 and 200° C., in addition to calcium phosphate. The described thermoplastic biocompatible polymer may be selected from: poly(lactic-co-glycolic acid), polylactic acid, polyglycolic acid, polyhydroxybutyrate, polyalkylene succinate, polybutylene diglycolate, polycaprolactone, and combinations thereof. The only examples disclosed relate to polylactic-glycolic acid, and the melting points of the tested mixtures are within a range greater than 100° C. The compositions described in this document require the use of very high temperatures to ensure their fluidity.

WO2010/0030220 discloses a system comprising a plurality of sections including a chamber forming a cement reservoir for the preparation of said cement, an injector in the form of a needle, and an activation chamber arranged between the reservoir chamber and the injector. The activation chamber is connected to a power source supplying the heating means comprised in the section corresponding to the activation chamber. The cement is composed of two components and a catalyst. The viscosity of the mixture is highly variable, and that document teaches heating the composition by means of the activation chamber and describes that a very significant but stable viscosity can be obtained through a loop for the temperature control of the mixture when polymerization is in progress. Such a system is complex and expensive to manufacture.

In particular, it should be noted that all documents cited above require the use of complex and expensive devices for heating and delivery of the composition.

Typically these are gun-type devices with reservoir and cannula, associated with an integrated heating and temperature control system which supplies sufficient heat to melt the bone substitute material and keep it fluid.

In such devices, the amount of heat is controlled either directly by the user or via an electronic feedback system in order to keep the material fluid. Such delivery devices generally comprise a handle, a housing, and a chamber for the material to be dispensed. These devices resemble a gun equipped with a reservoir for receiving the bone substitute type material as described above, a cannula, and means for heating and controlling the temperature (integrated or remote) of the material at the reservoir and at the beginning of the cannula in order to maintain the material in fluid form before it is injected into an implantation area.

These devices are complex in their manufacture, their use, and their maintenance. They are also expensive and heavy for a surgeon to handle. In addition, a wired electrical connection or a battery is needed to ensure the temperature control, which further complicates their use and/or poses an electrical hazard for the patient. Finally, their use involves steps of manipulating bone substitute type material in order to "load" the heating and extrusion chamber of the device. Such equipment can be used only with extemporaneous preparations of hardening polymer materials because their preparation, storage, and heating are carried out in different chambers or sections. In addition, after each use, such a gun-type device is discarded. At each use, the sterile gun-type device must be assembled and loaded with a dose of sterile filling material which is prepared, heated, and temperature-controlled. All these operations must be performed while maintaining sterility and asepsis, which for heavy and complex equipment is either very difficult or very expensive. As mentioned above, once used the device is discarded. Also, if the surgeon must interrupt the surgical procedure during use, the injection cannot be resumed because the polymerization is irreversible.

There is therefore a need for a new system of materials in new formats/delivery systems associated with new devices for their manipulation and their injection in the context of bone filling techniques under high mechanical stress, which solve the above problems while providing simplicity, ergonomics, ease of use for the surgeon as well as ensuring patient safety.

BRIEF SUMMARY OF THE INVENTION

Therefore a first object of the invention is to provide a bone filling composition packaged as a single-use dose, such as a rod or pellets, comprising or consisting of at least one resorbable or non-resorbable thermoplastic polymer material, characterized in that said composition has a viscosity between 40 and 4000 Pa·s, particularly between 50 and 3000 Pa·s, more particularly between 80 and 2500 Pa·s, even more particularly between 150 and 2000 Pa·s, between 200 and 1500 Pa·s and at a temperature of about 50° C. and a Young's modulus between 0.5 and 4 GPa, particularly between 1 and 4 GPa, between 1.5 and 3.5 GPa, even more particularly between 2 and 3 GPa, and this at about 37° C.

In the context of the invention, the term "single-use dose" is understood to mean that the amount of composition is suitable for surgery in a patient for at least one bone filling or for any type of surgery involving the addition of material to an area where bone is lacking. Single-use dose is also understood to mean that it is continuous and in single-use form and suitable for use in a device according to the invention as described below. It may be in the form of a rod or pellets of polymer material.

BRIEF DESCRIPTION OF THE DRAWING

The Figure describes a device comprising a syringe and external heating means structurally separate from the syringe.

DETAILED DESCRIPTION OF THE INVENTION

Figure 1:
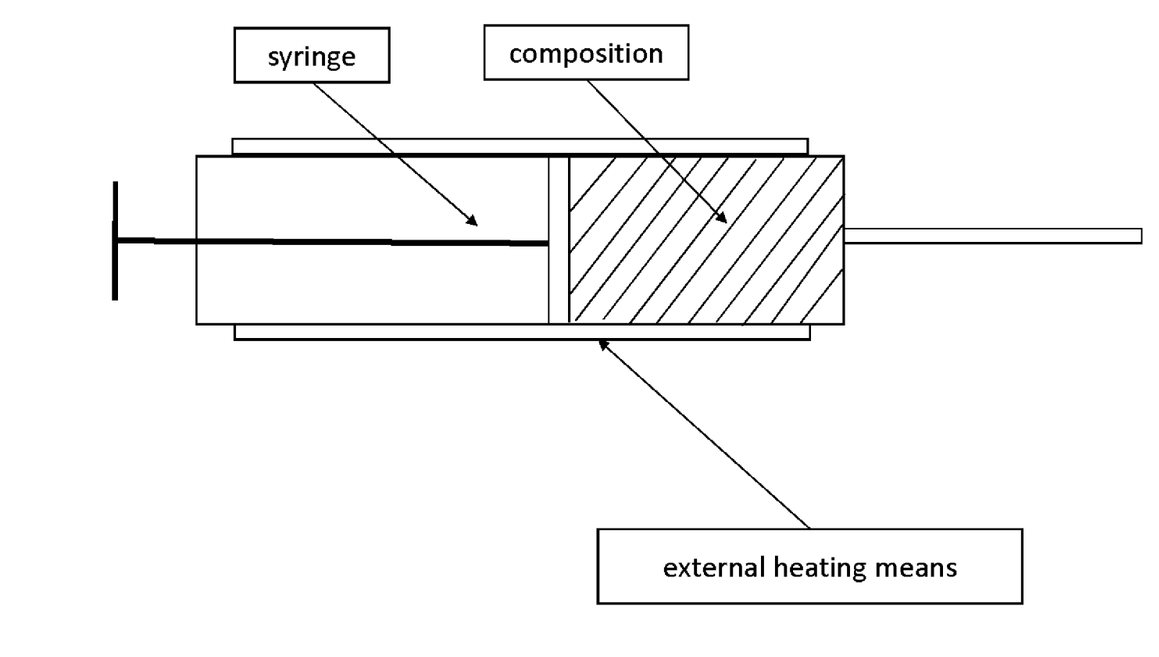

The polymer material may be resorbable or non-resorbable depending on the intended indications, and is thermoplastic. The polymer material is already polymerized and it is no longer necessary to perform an extemporaneous preparation of monomeric reactants and catalyst.

The resorbable or non-resorbable polymer material will be chosen according to its melting point, which will be between about 60° C. and 90° C.

This concept of melting temperature does not constitute a barrier as such. Materials having a melting point higher than 90° C. but still malleable at 60° C. may be suitable. Indeed, the inventors have observed that even if the polymer or the composition comprising it is heated to a temperature close to but less than the melting point, the polymer or the composition comprising it can be pushed out of the syringe and extruded through the cannula and injection needle.

Indeed, when coming close to the melting temperature, the "weak bonds" between the polymer chains become brittle under the influence of thermal agitation, and the polymer becomes soft and capable of deforming elastically or plastically without breaking. This property partly justifies the utility of most of the polymers according to the invention.

It is thus not necessary to be at the melting point (or beyond it), which may in fact exceed temperatures that are acceptable and compatible with patient tissues.

Advantageously, the resorbable or non-resorbable polymer material is a thermoplastic polymer.

The polymer material is chosen such that the composition has a viscosity between 40 and 4000 Pa·s, more particularly 50 and 3000 Pa·s, even more particularly between 80 and 2500 Pa·s, even more particularly between 150 and 2000 Pa·s, between 200 and 1500 Pa·s, and this at a temperature of about 50° C.

This feature reflects the fact that the composition is fluid or malleable at that temperature and can thus be easily extruded through a cannula and injected into an osseous point in a patient, with no risk of burning or necrosis of the patient's tissue.

In addition, the polymer material of the composition is such that said composition has, after cooling and more particularly at a temperature of about 37° C., a hardness such that the Young's modulus of said composition is between 0.5 and 4 GPa, particularly between 1 and 4 GPa, between 1.5 and 3.5 GPa, even more particularly between 2 and 3 GPa, and this at about 37° C.

The term "fluid or malleable" is thus understood to mean a composition which is flowable or soft, its viscosity between the values indicated above, i.e. between 40 and 4000 Pa·s, at a temperature of about 50° C. and is therefore extrudable and injectable. The composition made "fluid or malleable" by heating can thus pass through a cannula of a diameter between 8 gauge and 15 gauge. Heating the composition to a temperature close to or above the polymer melting point enables the fluidization, or at least softening, of said composition, thus enabling it to advance through the cavity of a cannula by the application of pressure in order to inject it.

For some polymers having a melting point higher than 50° C. or 60° C., for example about 80, 90, or 100° C., it has been observed that these could be heated to about 100 or 120° C. in order to reach or exceed the melting point and then slowly cooled to about 50 or 60° C., and that they retain a malleability enabling their extrusion and injection from the syringe and through the needle without excessive effort.

The Young's modulus of the composition after cooling, in particular at 37° C., is advantageously between 2 and 3 GPa.

The Young's modulus or (longitudinal) elasticity module or tensile modulus is the constant that makes the link between the tensile (or compression) stress and the beginning of deformation of a material.

The law of elasticity is Hooke's law, in other words σ=E ε where:
σ is the stress (in units of pressure);
E is the Young's modulus (in units of pressure);
ε is the relative elongation, or strain (dimensionless).

The Young's modulus is the mechanical stress that would cause 100% elongation of the original length of a material (therefore doubling it in length), if this could actually be applied: in actuality, the material deforms permanently or breaks long before this value is reached. The Young's modulus is the initial slope of the stress-strain curve.

A material having a high Young's modulus is said to be rigid. The Young's modulus can be measured according to DIN/EN/ISO 527-2 for example.

Such rigidity ensures a high mechanical strength of the composition after implantation in a bone cavity and thus constituting a bone implant that is permanent or resorbable depending on the nature and quality of the components of the composition.

The selection of the resorbable or non-resorbable thermoplastic polymer material falls under the conventional practices and measures for those skilled in the art, based on physicochemical characteristics (for example melting point) and rheological characteristics which are either known or measurable using laboratory techniques within their reach.

"Bone implant" is understood herein to mean any material used to assist or enhance defective bone formation. Bone implants are often applied to fill and supplement bone loss resulting from an injury, malformation, deformity, deficiency, or surgery for example. A bone implant can be used in a variety of surgeries, whether orthopedic surgery or neurosurgery for example.

The polymer material of the composition according to the invention may be a resorbable thermoplastic polymer and may be selected from the group consisting of poly(lactic-co-glycolic acid), polylactic acid (PLA), polyglycolic acid (PLGA), polycaprolactone (PCL), polyhydroxybutyrate, poly(glycerol sebacate), polydioxanone, used alone or in admixture. Preferably it is selected from poly(lactic-co-glycolic acid), polylactic acid (PLA), polyglycolic acid (PLGA), polycaprolactone (PCL), alone or in admixture.

The resorbable thermoplastic polymer may be a physical mixture or chemical mixture of the compounds mentioned above. Thus chemical mixture can be understood to mean PCL-PLA or PCL-PGA or PCL-PLGA copolymers. Physical mixture is understood to mean a mixture comprising polymers, for example PCL PLA, but the monomer units are not linked by covalent bonds as is the case with copolymers. PCL-PLA, PCL-PGA, PCL-PLGA physical mixtures in varying ratios can thus be contemplated. The advantage of integrating PCL in a mixture containing PLA or PGA or PLGA is to lower the melting point of PLA or PGA or PLGA and maintain rigidity once the mixture is cooled.

The polymer of the composition according to the invention may be a non-resorbable thermoplastic polymer selected from the group consisting of polymers and copolymers of acrylates and methacrylate, polyurethane, polyethylene, alone or in admixture, preferably from polymers and copolymers of acrylates and methacrylate.

Among the polymers and copolymers of acrylates and methacrylate C6-C18 alkyl polymethacrylates or a mixture thereof can be selected, for example polystearylmethacrylate, which have lower melting point than polymethylmethacrylate for example. Thus, physical mixtures of C1-C18 alkyl polymethacrylates having variable amounts of polymers with more or less long side chains can be prepared. Such physical mixtures make it possible to obtain mixtures of thermoplastic polymers having a melting point close to 100° C. while maintaining the desired stiffness.

In one particular embodiment, the polymer is a resorbable thermoplastic polymer and is polycaprolactone alone or mixed with another resorbable thermoplastic polymer.

In one particular embodiment, the polymer is a polycaprolactone having a molecular weight between 10,000 and 100,000, particularly between 30,000 and 60,000, more particularly between 30,000 and 50,000, even more particularly around 40,000.

The molecular weight of polycaprolactone determines the melting point of the polymer and therefore of the composition. The higher the molecular weight, the lower the melting point. However, this molecular weight also determines the stiffness of the material at a temperature of about 37° C., i.e. body temperature. Thus a low molecular weight causes brittleness of the cured material, which is not acceptable. On the other hand, the viscosity of the material heated above its melting point is largely determined by its molecular weight. Also, the viscosity is proportional to the molecular weight.

A polymer with viscosity in the molten state or in the malleable state enabling extrusion and injection of the composition at a temperature of about 50° C. and without excessive effort, while presenting a temperature compatible with the patient's biological tissues, can be chosen.

Finally, the mechanical strength and stiffness of the composition once in place and cooled to body temperature should be high enough to fulfill its role as filling material and to withstand the mechanical stresses.

The polymer can therefore be chosen by the skilled person using routine tests consisting in measuring the melting temperature and the associated viscosity and retaining the polymers which makes it possible to obtain a composition having a viscosity as indicated above, at a temperature of about 50° C.

A second criterion for selecting a suitable polymer consists in measuring the Young's modulus of the composition comprising or consisting of the polymer, and retaining the one which makes it possible to obtain a Young's modulus for the composition of between 0.5 and 4 GPa, particularly between 1 and 4 GPa, between 1.5 and 3.5 GPa, even more particularly between 2 and 3 GPa, and this at about 37° C.

In another embodiment, the composition in the form of a single-use dose, such as a rod or pellets, according to the invention further comprises an inorganic material, particularly an inorganic biomaterial, more particularly a calcium phosphate biomaterial.

Also, the weight ratio of polymer/inorganic material of the composition according to the invention may be between 100/0 and 40/60 for example, particularly between 90/10 and 50/50, more particularly between 80/20 and 70/30.

This ratio also influences the viscosity of the composition at the time of injection as well as the strength of the solidified composition, meaning of the bone implant, once arranged in the cavity which is filled. The ratio will be determined in conjunction with the nature of the polymer as well as the viscosity of said polymer and its hardness, such that the viscosity of the composition at 50° C. is between 40 Pa·s and 4000 Pa·s and such that the Young's modulus of the composition at about 37° C. is between 0.5 and 4 GPa, particularly between 1 and 4 GPa, between 1.5 and 3.5 GPa, more particularly between 2 and 3 GPa.

The single-use dose of the composition according to the invention is sized to correspond to one or more bone fillings and is between 2 and 50 ml, preferably between 4 and 12 ml.

Advantageously, the single-use dose is in the form of a rod of cylindrical cross-section whose dimensions may be about 4 to 10 cm long and 1 to 3 cm in diameter. This format allows the use of such a dose in a device as discussed further below in the description.

In another embodiment, the single-use dose may be in the form of pellets and the quantity of these pellets present in the syringe corresponds to the filling dose.

According to one embodiment, the calcium phosphate biomaterial type of inorganic material is a calcium phosphate bioceramic, particularly a strontium-containing calcium phosphate bioceramic.

The calcium phosphate material, such as a calcium phosphate bioceramic, offers the advantage of being bioresorbable.

Preferably, said bioceramic comprises or consists of one or more sintered calcium phosphate compounds selected from the group consisting of hydroxyapatite (HA), alpha- and beta-tricalcium phosphate (α-TCP, β-TCP), and biphasic calcium phosphate material (BCP) or one of their mixtures.

It is particularly preferred that said bioceramic comprises a biphasic calcium phosphate material, comprising or consisting of about 80% HA and about 20% TCP or about 20% HA and about 80% β-TCP.

In one embodiment, the inorganic base material is a resorbable calcium phosphate biomaterial. In particular, the calcium phosphate biomaterial is supplemented by the substitution of one or more calcium atoms with strontium atoms. The addition of a strontium atom proportionally increases the radiopacity of the final biomaterial.

The calcium phosphate biomaterial type of inorganic compound may be selected from the group comprising amorphous calcium phosphate (ACP), $Ca_x(PO_4)y·H_2O$; monocalcium phosphate monohydrate (MCPH), $CaH_4(PO_4)_2·H_2O$; dicalcium phosphate dihydrate (DCPD), $CaHPO_4·2H_2O$; anhydrous dicalcium phosphate (DCPA), $CaHPO_4$; precipitated or calcium-deficient apatite (CDA), $(Ca,Na)_{10}(PO_4,HPO_4)_6(OH)_2$; alpha- or beta-tricalcium phosphate (α-TCP, β-TCP), $Ca_3(PO_4)_2$; and tetracalcium phosphate (TTCP), $Ca_4P_2O_9$.

More specifically, the composition according to the invention in the form of a single-use dose is in the form of a rod or pellets, and comprises 40 to 100 wt.% of a polycaprolactone polymer having a molecular weight between 10,000 and 100,000, more particularly between 30,000 and 60,000, and 0 to 60% of a calcium phosphate biomaterial, in particular a calcium phosphate biomaterial comprising hydroxyapatite and/or tricalcium phosphate.

Advantageously, the polycaprolactone polymer is resorbable.

Advantageously, the ratio by weight of hydroxyapatite/tricalcium phosphate in the calcium phosphate biomaterial is between 80/20 and 20/80, more advantageously between 65/35 and 35/65.

According to a particularly advantageous embodiment of the invention, the calcium phosphate biomaterial according to the invention comprises 65 wt. % hydroxyapatite and 35 wt. % strontium-containing tricalcium phosphate.

The inorganic material of the composition according to the invention may also be selected from the group consisting of bioglasses, silicates, in particular aluminosilicates, calcium sulfates, and barium sulfates.

The composition according to the invention may comprise organic molecules and compounds such as polysaccharides, proteins, or peptides, lipids for example.

The compositions according to the invention have great utility for the new surgical techniques that are in increasing use, for example such as vertebroplasty or kyphoplasty, or more generally osteoplasty.

These operations require materials that are radiopaque in nature (permanently or not depending on the case). They are indeed carried out in vertebrae that are fractured to a greater or lesser extent and a leakage of material to outside the vertebrae can be critical, resulting in neurological and vascular complications that can lead to death. It is therefore advantageous for the surgeon to be able to observe the amount of injected product, its dispersion in the vertebra, and in particular to check that the material remains inside the vertebra.

According to the invention, radiopaque agents for medical X-ray imaging can be added to the compositions according to the invention. These may be iodinated, ionic or nonionic compounds such as Iomeron® or Iopamidol®. These iodinated solutions render the gel completely radiopaque and thus makes it possible to be detected by X-ray radiography. Strontium-stabilized derivatives can also be envisaged as mentioned above.

In the case of resorbable products, the radiopaque agents and compounds present in the composition, once injected, have the additional advantage of disappearing over time, which allows assessing the efficacy of the bone reconstruction.

In addition, the compositions according to the invention have exceptional rheological properties after heating.

They form viscous products of thick structure in the form of a paste that is injectable through a cannula at a temperature of about 50° C. at the outlet of said cannula.

The invention also relates to the use of compositions according to the invention as a bone substitute for vertebroplasty.

The invention also relates to the method for preparing the compositions described above. Such a method comprises the following successive steps:
 preparing a homogeneous mixture comprising the resorbable or non-resorbable thermoplastic polymer, particularly a resorbable thermoplastic polymer of the polycaprolactone type having a molecular weight between 10,000 and 100,000, and optionally an inorganic material;
 The mixture is achieved by a controlled mechanical or chemical process;

The mixture makes it possible to obtain shapes such as a rod after passage through an injection press. Alternatively, the mixture may be formulated as pellets.

Sterilization of the obtained product may be carried out by means known to those skilled in the art, for example with ethylene oxide.

Another purpose of the invention also resides in a syringe type device containing the composition according to the invention, for the injection of said composition into an osseous point in order to perform bone filling.

In particular, the invention therefore relates to an assembly composed of a syringe and a single-use dose of a composition according to the invention, said syringe being prefilled with said single-dose composition according to the invention, said syringe enabling both the storage and administration of said composition, said syringe further comprising a syringe body having an opening at each of its two ends, the first opening bearing sealing means for sealing it closed, in particular a plug, and/or means for the administration of said composition, in particular a cannula, the second opening being sealed closed by sealing means, in particular a piston seal, slidable inside the syringe body, in particular by means of a piston rod, in particular connected to said slidable sealing means, said syringe body, said sealing and/or administration means, and said slidable sealing means defining a volume within which said composition is contained.

An object of the present invention is a therefore a device comprising:
  a prefilled syringe containing a single-use dose of a composition for bone filling, such as a rod or pellets, said composition comprising at least one resorbable or non-resorbable thermoplastic material, said composition having a viscosity between 40 and 4000 Pa·s at a temperature of about 50° C. and a Young's modulus between 0.5 and 4 GPa at about 37° C., said syringe enabling both the storage and administration of said composition, said syringe comprising a syringe body having an opening at each of its two ends, the distal first opening bearing sealing means for sealing it closed, in particular a plug, and/or means for the administration of said composition, in particular a cannula, the proximal second opening being sealed closed by sealing means, in particular a piston seal, slidable inside the syringe body, in particular by means of a piston rod adapted to be moved toward the distal opening, in particular connected to said slidable sealing means, said syringe body, said sealing and/or administration means, and said slidable sealing means defining a volume within which said dose is contained;
  an external heating means structurally separate from the syringe and making it possible to heat it and melt or soften the dose of the composition for bone filling for the purposes of its administration.

The syringe body according to the invention may be made of any material that is heat-resistant at a temperature between 80 and 150° C. or even 120° C.; and in particular the syringe body is made of metal. A particularly suitable metal is aluminum, because of its lightness and its thermal inertia allowing good thermal conductivity.

The piston rod may be a threaded rod which can be used to advance the composition after heating and fluidification, by screwing said piston rod. In this case, the end through which the piston rod passes may be provided with a thread complementary to the thread of the piston rod.

The use of prefilled syringes according to the invention enables practitioners to avoid the steps of extemporaneous preparation and transfer of the filling product from its container to a delivery device as mentioned above, which, beyond improving ease of use, ensures better product sterility.

Indeed, the use of a prefilled syringe enables disposability, which facilitates handling and reduces the risk of an incorrect dosage.

According to one advantageous embodiment, the invention relates to an assembly according to the invention as described above, wherein the volume of the single-use dose of the composition stored in the syringe is between 1 and 50 ml, preferably between 2 and 35 ml, more preferably between 4 and 20 ml.

The term single-use dose in the context of the present invention is understood to mean that the amount of composition is suitable for surgery in a patient for at least one bone filling or for any type of surgery involving the addition of material in a location where bone is missing. This single-use dose is also understood to be continuous and in disposable form and suitable for use in a device according to the invention. This dose may be in the form of a rod of resorbable polymer material occupying the internal volume of the syringe, but it may also be beads or pellets of said material.

The volume of said single-use dose of the composition is less than or equal to the maximum volume that said syringe can contain. According to a particularly advantageous embodiment, the invention relates to an assembly as described wherein the volume of the single-use dose of said composition, stored in said syringe, is between 1 and 20 ml, preferably between 2 and 10 ml, more preferably between 4 and 10 ml. According to another particularly advantageous embodiment, the present invention relates to a device wherein the volume of the single-use dose of said composition, stored in said syringe, is between 10 and 50 ml, preferably between 10 and 35 ml, more preferably between 10 and 20 ml.

According to a particularly advantageous embodiment, the invention relates to an assembly wherein the means for administration of the composition is or are end-joined to the end of the syringe body and comprise or consist of a cannula whose diameter is between 8 gauge and 15 gauge, in particular 10 gauge to 14 gauge.

The volume of the syringe can be changed by sliding said sealing means within the body, in the direction of the distal first opening, said opening being in particular without sealing means. When the distal first opening bears sealing means, in particular a plug, and administration means, in particular a cannula, said sealing means, initially fluidtight, are then pierced as said administration means are put in place. In this case, it is not necessary to replace said sealing means with said administration means in order to administer said composition. A piston rod can be adapted to said piston seal to allow administration of said composition, said administration being manual or being carried out by automated administration means.

In one particular embodiment, the prefilled syringe according to the invention, with or without administration means, is heated to a temperature close to or higher than the melting point of the composition for bone filling that is contained in the body of the syringe.

This heating can be done by any suitable means known to the skilled person but which is external and structurally separate from the syringe. This feature of the device according to the invention makes it possible to have a means for the storage and administration of the composition, i.e. the syringe, devoid of any integrated electrical or electronic heating systems as known from the prior art. This configuration makes it possible to have a system that is simple, economic, and robust to manufacture and use. In particular, prior to use, the prefilled syringe, equipped or not equipped with administration means, can be placed in a temperature-controlled heating chamber at a temperature between 80° C. and 150° C., particularly between 80° C. and 120° C., more particularly between 80 and 90° C. It is also possible to heat the syringe with a sheath or collar heater of a type sized to receive the syringe body with or without the injection cannula.

This heating makes it possible to approach, reach, or exceed the melting point of the thermoplastic polymer material and to make the composition sufficiently malleable or fluid for easy extrusion and injection. Depending on the nature of the polymer or the mixture containing the thermoplastic polymer, it is possible to leave the device for a certain amount of time in the heating system in order to make the composition sufficiently fluid. Once this state of fluidity or malleability is achieved, the inventors have noted a hysteresis such that, when cooling, the viscosity is always lower - for a given temperature—than the viscosity observed during the increase in temperature. This makes it possible to obtain a malleable composition that is extrudable and injectable at about 50° C. after being heated to 90° C. or 100° C., i.e. close to the melting point of the polymer.

The syringe is therefore used as a storage medium or heat transfer reservoir.

In one particular embodiment, the external heating means structurally separate from the syringe may be an oven suitable for regulating the temperature of the syringe containing the composition of the invention and is in the form of a cylinder having a diameter substantially equal to but slightly larger than that of the syringe in order to enable insertion of the syringe into the body of said oven. Similarly, the length of this cylinder will be substantially equal to or slightly greater than the length overall of the assembly according to the invention. As the assembly may or may not include a cannula joined at one end, the length of the cylinder of the oven may be such that it is at least equal to the length of the syringe including the cannula, if provided, in order to heat said cannula.

It is also a purpose of the invention to provide a device according to the invention wherein the heating means comprises an oven which is in the form of a heating cylinder having a diameter substantially equal while being slightly greater than that of the syringe in order to enable insertion of the syringe into the body of the chamber and having a length substantially equal to or slightly greater than the length of the device, with or without the joined cannula.

The heating cylinder of the oven may be equipped with electrical heating resistors ensuring the increase in temperature, or any other means for achieving this increase in temperature, for example induction.

Indeed, the melting point of the resorbable or non-resorbable thermoplastic polymer material of the composition for bone filling according to the invention falls between 50 and 120° C., particularly between 50° C. and 90° C., more particularly between 50 and 70° C., depending on the nature of the polymer, the molecular weight of the polymer, more particularly the resorbable polymer of polycaprolactone, as well as the amount of this polymer, or the ratios of polymers in the case of a physical mixture, in said composition. As mentioned above, the higher the molecular weight, the higher the melting temperature. In addition, the presence of a calcium phosphate biomaterial type of inorganic compound in the composition will tend to lower the melting or softening temperature of the composition comprising the thermoplastic polymer. This makes it possible to use polymers with melting temperature within a range of about 100° C. or even higher.

Thus, the regulated temperature of the assembly according to the invention, i.e. of the syringe containing the single-use dose of the composition for bone filling, is determined by the volume and nature of said composition.

As mentioned above, a regulated temperature of the assembly according to the invention of around 90° C. for a period of about 3 to 20 minutes for example, enabling a temperature of about 80° C. at the core of the single-use dose of the composition, thus enables fluidization of said composition contained in the syringe body compatible with injection, in particular into the patient's vertebral body through suitable tubing. This core temperature can of course be adapted to the nature of the composition used.

Indeed, this temperature (about 80° C.) is certainly not compatible with tissue, but given the heat transfers and losses as well as the temperature gradient within the parts of the device at the time of injection, the temperature of the cannula in contact with tissue will be about 50° C. and the temperature of the composition in the needle as well as at the injection site (for example the vertebra) will also be of this order of magnitude, which will avoid tissue burning.

In addition, at this temperature (about 50 to 60° C.) within the composition comprised in the needle, the composition is fluid and the needle can therefore be removed without difficulty. Indeed, as indicated above, the first end of the syringe body is equipped with means for dispensing the composition, in particular a surgical cannula.

The length of the cannula can be chosen according to the desired application and will be about 100 to 150 mm.

Typically, during extrusion of the fluidized composition by applying force on the piston rod, the advancement of the fluid composition along the cannula implanted in the patient's body causes the composition to cool. Similarly, once the composition reaches the cavity to be filled, a temperature decrease is also observed.

It is therefore necessary to anticipate a suitable temperature of the composition within the syringe body so that after its advancement along a cannula arranged in a bone cavity of the patient, via a trocar, and at the mouth of said cavity, the composition will not have solidified. Thus, a preferred temperature of the composition according to the invention of about 80° C. in the body of the syringe makes it possible to obtain a fluid and injectable composition which remains fluid when it has reached the end of a 150 mm cannula, its temperature then being 45 to 50° C.

At the opening into the bone cavity, in contact with the patient's internal medium, the temperature of the composition is at about 40 to 45° C. which enables said composition, still more or less fluid, to fill the void effectively.

Such a temperature profile makes it possible to reconcile effective injection and delivery and to protect the patient's tissues from any risk of necrosis.

An object of the invention also relates to a kit comprising an assembly according to the invention and a cannula for injecting the composition.

At the moment when the assembly or kit according to the invention is implemented, the plug of the end of the syringe is removed, a cannula, particularly the one included in the kit, is attached to said end, and the assembly is set to heat in a suitable heating device such as for example a cylindrical oven as mentioned above.

In the case of using the composition in vertebroplasty, during heating of the assembly, the surgeon will be able to proceed with positioning a trocar at the vertebra that is fractured or is to be treated for example. This can be done safely under continuous radiographic monitoring during the surgery. A balloon may then be inserted through the trocar into the vertebra and inflated. This thus restores the vertebra, which is raised to form a cavity. After removing the balloon, the cannula of the syringe is inserted into the trocar and the composition is extruded to fill the cavity with the filling composition.

The composition is completely hard after a few minutes or tens of minutes depending on the nature and amount of thermoplastic polymer.

The syringe body is preferably made of metal, particularly aluminum which enables a rapid heat transfer to the interior and enables liquefaction of the contained composition while ensuring sufficient thermal inertia to maintain the composition in a melted state and at a satisfactory viscosity for extrusion.

In addition, if the surgeon wishes to increase the fluidity of the composition contained in the syringe and/or cannula during administration, it is sufficient to reintroduce it into the heating means to liquefy said composition for the purpose of its dispensing.

In one particular embodiment, and in order to facilitate handling of the syringe by the surgeon, an insulating sheath completely or partially surrounding the syringe and the composition administration and/or sealing means is arranged on the syringe body.

This sheath may be integral with the syringe body or may be removable.

This sheath, integral or removable, is slidable along the longitudinal axis of the syringe body and may totally or partially cover said body, locking in place and retaining the syringe body while enabling the piston rod to advance, for example by screwing or simply pushing. Such a sheath protects the surgeon or any person handling the syringe from burns due to the temperature of the syringe body when it exits the heating device. The sheath may also for example be in the form of two half shells connected by a hinge which clamp around the syringe and retain it.

Indeed, at the time of introduction of the assembly into a heating device, the insulating sheath is slid, or removed, so that it no longer covers the syringe body which is thus heated independently of said sheath. Once the syringe body is brought to the desired temperature, said sheath is slid in the opposite direction so that it covers the syringe body. In the case of a removable sheath, the sheath is repositioned on the syringe body. This sheath may be locked in one or both of the sliding positions, preferably in the position completely covering the syringe body in order to enable said body to be gripped and the contained composition to be pushed out. The locking may be achieved through a bayonet system via a push-and-rotate motion for example.

The insulating protective sheath may be composed of any material as long as it is a poor heat conductor or even is a thermal insulator. It may be for example of silicone resin or polycarbonate polymer or any other material of low thermal conductivity.

The present invention eliminates the steps of extemporaneous preparation of cements or of handling materials in pellet form which are introduced into a heating chamber of a heating gun.

The assembly according to the invention, a prefilled syringe, can be packaged and sterilized and can be used directly in the operating theater while minimizing the handling involved.

In addition, after heating and during handling, if the composition contained in the syringe body or already present in the cannula solidifies, one simply needs to place the assembly back in the external heating means, such as a chamber or heating sheath, to reheat it in order to fluidize the composition once again, and then resume the injection.

This advantage is not possible with the existing heat gun types of devices because the associated cannula is not heated and when the composition contained therein is solidified, this cannula must be removed and the heating restarted.

The system according to the invention has the advantage of comprising a syringe that is structurally separate from any heating means or external energy once it has been heated to the appropriate temperature, which makes it a self-contained heat transfer system. Thus the absence of any battery, electrical resistors, electrical wires for connection to an external power source enables the surgeon to easily manipulate it and eliminates any electrical hazard for the patient. Finally, the mechanically simple design of the system according to the invention makes mass production possible, at a competitive price.

A system according to the invention therefore has the advantage of being easy to handle, easy and inexpensive to manufacture, and disposable after use.

EXAMPLE 1

Measurement of Rheological Properties

The used equipment consists of:
MCR51 rheometer
3-EC-02 climate chamber (SLH 100—Secasi)
RheoPlus software The tests for measuring the viscosity of the polycaprolactone polymer are carried out using an Anton Paar MCR51 rheometer/viscometer in dynamic shear mode (1 Hz). This apparatus makes it possible to record the evolution of the complex viscosity over time and at a constant temperature. In order to approximate the actual usage conditions of the heating injector, the polymer is melted at 90° C. in the apparatus and then a temperature setpointwas fixed (temperature at which the material will reach the bone site to be filled). The measurement acquisition is begun when the desired temperature (50° C.) of the support is stable.

EXAMPLE 2

Composition of PCL+strontium-containing calcium phosphate
PCL with molecular weight Mn=30,000 g/mol β-TCP strontium
Ratio PCL/calcium phosphate agent
PCL/β-TCP (Sr)=70/30
Particle size of calcium phosphate agent
B-TCP(Sr)=30 μm
Injection device/syringe
Injection device according to the invention with a metal cartridge filled with a rod of PCL/TCP(Sr) connected to an 11 gauge cannula insertable into a 10 gauge trocar. The device was heated in a temperature-regulated heating chamber at 90° C. before its transfer for injection into the vertebra.

The invention claimed is:

1. A device comprising:
a syringe prefilled with a single-use dose of a composition for bone filling,
   wherein said composition comprises at least one resorbable or non-resorbable thermoplastic polymer material,
   wherein said composition has a viscosity between 40 and 4000 Pa·s at a temperature of about 50° C. and a Young's modulus between 0.5 and 4 GPa at about 37° C.,
   wherein said composition is in the form of a rod or pellets and comprises by weight 40 to 100% of a polycaprolactone polymer having a molecular weight between 30,000 and 60,000, and 0 to 60% of a calcium phosphate biomaterial,
   wherein said syringe enables both the storage and administration of said composition,
   wherein said syringe comprises:
      a syringe body having an opening at each of its two ends,
      a distal first opening bearing sealing means for sealing it closed and/or means for the administration of said composition, and
      a proximal second opening being sealed closed by sealing means slidable inside the syringe body,
      wherein said syringe body, said sealing and/or administration means, and said slidable sealing means define a volume within which said dose is contained; and
   an external heating means structurally separate from the syringe and making it possible to heat it and melt or soften the dose of the composition for bone filling for the purposes of its administration.

2. The device according to claim 1, wherein the syringe body is made of metal.

3. The device according to claim 2, wherein the heating means comprises an oven suitable for regulating the temperature of said device, said oven in the form of a heating cylinder having a diameter substantially equal to but slightly greater than that of the syringe in order to allow insertion of the syringe into the body of the oven and having a length substantially equal to or slightly greater than the length overall of the device.

4. The device according to claim 1, wherein the volume of the single-use dose of the composition stored in the syringe is between 1 and 50 ml.

5. The device according to claim 4, wherein the heating means comprises an oven suitable for regulating the temperature of said device, said oven in the form of a heating cylinder having a diameter substantially equal to but slightly greater than that of the syringe in order to allow insertion of the syringe into the body of the oven and having a length substantially equal to or slightly greater than the length overall of the device.

6. The device according to claim 1, wherein the means for administration of the composition are joined to the end of the syringe body and comprise a cannula the diameter of which is between 8 gauge and 15 gauge.

7. The device according to claim 6, wherein the heating means comprises an oven suitable for regulating the temperature of said device, said oven in the form of a heating cylinder having a diameter substantially equal to but slightly greater than that of the syringe in order to allow insertion of the syringe into the body of the oven and having a length substantially equal to or slightly greater than the length overall of the device.

8. The device according to claim 1, wherein the thermoplastic polymer material is a resorbable polymer and is selected from the group consisting of poly(lactic-co-glycolic acid), polylactic acid, polyglycolic acid, polycaprolactone, polyhydroxybutyrate, poly(glycerol sebacate), poly(dioxanone), alone or in admixture.

9. The device according to claim 8, wherein the heating means comprises an oven suitable for regulating the temperature of said device, said oven in the form of a heating cylinder having a diameter substantially equal to but slightly greater than that of the syringe in order to allow insertion of the syringe into the body of the oven and having a length substantially equal to or slightly greater than the length overall of the device.

10. The device according to claim 1, wherein the thermoplastic polymer material is a non-resorbable polymer and is selected from the group consisting of polymers and copolymers of acrylates and methacrylate, polyurethane, polyethylene, alone or in admixture.

11. The device according to claim 10, wherein the heating means comprises an oven suitable for regulating the temperature of said device, said oven in the form of a heating cylinder having a diameter substantially equal to but slightly greater than that of the syringe in order to allow insertion of the syringe into the body of the oven and having a length substantially equal to or slightly greater than the length overall of the device.

12. The device according to claim 1, wherein the composition further comprises an inorganic material.

13. The device according to claim 12, wherein the calcium phosphate biomaterial is a calcium phosphate bioceramic.

14. The device according to claim 13, wherein the bioceramic comprises or consists of one or more sintered calcium phosphate compounds selected from the group consisting of hydroxyapatite (HA), alpha- and beta-tricalcium phosphate ($\alpha$-TCP, $\beta$-TCP), and biphasic calcium phosphate material (BCP), alone or in admixture.

15. The device according to claim 1, wherein the weight ratio of polymer/inorganic material of the composition is between 100/0 and 40/60.

16. The device according to claim 1, wherein an insulating sheath completely or partially surrounding the syringe and the composition administration and/or sealing means is arranged on the syringe body.

17. The device according to claim 1, wherein the heating means comprises an oven suitable for regulating the temperature of said device, said oven in the form of a heating cylinder having a diameter substantially equal to but slightly greater than that of the syringe in order to allow insertion of the syringe into the body of the oven and having a length substantially equal to or slightly greater than the length overall of the device.

* * * * *